(12) United States Patent
Bielenstein et al.

(10) Patent No.: US 11,291,548 B2
(45) Date of Patent: Apr. 5, 2022

(54) DENTAL SCREW

(71) Applicant: Botiss Biomaterials GmbH, Zossen (DE)

(72) Inventors: Oliver Bielenstein, Berlin (DE); Drazen Tadic, Berlin (DE); Frank Witte, Berlin (DE); Romano Matthys, Horgen (CH)

(73) Assignee: Botiss Biomaterials GmbH, Zossen (DE)

( * ) Notice: Subject to any disclaimer, the term of this patent is extended or adjusted under 35 U.S.C. 154(b) by 173 days.

(21) Appl. No.: 16/642,109

(22) PCT Filed: Aug. 28, 2018

(86) PCT No.: PCT/EP2018/073094
§ 371 (c)(1),
(2) Date: Feb. 26, 2020

(87) PCT Pub. No.: WO2019/042974
PCT Pub. Date: Mar. 7, 2019

(65) Prior Publication Data
US 2020/0179120 A1 Jun. 11, 2020

(30) Foreign Application Priority Data
Aug. 28, 2017 (DE) .................... 10 2017 119 657.9

(51) Int. Cl.
*A61F 2/28* (2006.01)
*A61C 8/00* (2006.01)
*A61F 2/30* (2006.01)
*A61B 17/86* (2006.01)
*A61B 17/88* (2006.01)
*A61B 17/16* (2006.01)

(52) U.S. Cl.
CPC ...... *A61F 2/30749* (2013.01); *A61B 17/8605* (2013.01); *A61B 17/8635* (2013.01); *A61B 17/8863* (2013.01); *A61F 2/2803* (2013.01); *A61B 17/1673* (2013.01); *A61F 2002/30062* (2013.01); *A61F 2310/00041* (2013.01); *A61F 2310/00065* (2013.01); *A61F 2310/00083* (2013.01); *A61F 2310/00592* (2013.01)

(58) Field of Classification Search
None
See application file for complete search history.

(56) References Cited

U.S. PATENT DOCUMENTS 5,713,903 A * 2/1998 Sander ................ A61F 2/0811
606/326
5,876,435 A * 3/1999 Swords .............. A61B 17/8615
623/4.1
(Continued)

FOREIGN PATENT DOCUMENTS

CN 1208354 A 2/1999
CN 1565389 A 1/2005
(Continued)

*Primary Examiner* — Ann Schillinger
(74) *Attorney, Agent, or Firm* — Smartpat PLC (57) ABSTRACT

A screw suitable for use specifically in the field of oral dental surgery consists of a bioresorbable material and comprises a drive that can be broken off by means of a predetermined breaking point and/or has a thickened shaft below the contact surface of a cap of the head of the screw.

18 Claims, 5 Drawing Sheets

(56) References Cited

U.S. PATENT DOCUMENTS

| | | | |
|---|---|---|---|
| 5,928,236 A | 7/1999 | Augagneur et al. | |
| 5,971,987 A | 10/1999 | Huxel et al. | |
| 6,007,539 A | 12/1999 | Kirsch et al. | |
| 6,096,060 A | 8/2000 | Fitts et al. | |
| 6,723,099 B1 | 4/2004 | Goshert | |
| 2001/0034524 A1* | 10/2001 | Bales | A61B 17/725 606/62 |
| 2003/0153975 A1* | 8/2003 | Byrd, III | A61F 2/447 623/17.11 |
| 2005/0152770 A1* | 7/2005 | Tschakaloff | F16B 33/006 411/403 |
| 2006/0081553 A1* | 4/2006 | Patterson | A61B 17/8014 215/252 |
| 2007/0141110 A1* | 6/2007 | Stone | A61B 17/866 424/423 |
| 2007/0218750 A1 | 9/2007 | Corrao et al. | |
| 2007/0270859 A1 | 11/2007 | Companioni et al. | |
| 2007/0287129 A1 | 12/2007 | Ihde | |
| 2008/0140118 A1* | 6/2008 | Martinek | A61B 17/0625 606/232 |
| 2010/0191294 A1 | 7/2010 | Zergiebel | |
| 2011/0313527 A1 | 12/2011 | Witte et al. | |
| 2012/0214127 A1 | 8/2012 | Drapeau et al. | |
| 2013/0079829 A1 | 3/2013 | Globerman et al. | |
| 2013/0261671 A1 | 10/2013 | Horvath | |
| 2014/0303676 A1* | 10/2014 | Stroncek | A61B 17/888 606/304 |
| 2019/0365443 A1 | 12/2019 | Zeng | |

FOREIGN PATENT DOCUMENTS

| | | |
|---|---|---|
| CN | 102170921 A | 8/2011 |
| CN | 202477833 U | 10/2012 |
| CN | 203988332 U | 12/2014 |
| CN | 105167830 A | 12/2015 |
| CN | 106730043 A | 5/2017 |
| DE | 3630863 A1 | 3/1988 |
| DE | 3701765 C1 | 6/1988 |
| DE | 10065799 C1 | 4/2002 |
| DE | 69528501 | 7/2003 |
| DE | 102010055433 A1 | 6/2012 |
| DE | 102014008449 A1 | 12/2015 |
| DE | 102015009932 A1 | 2/2017 |
| FR | 2625430 A1 | 7/1989 |
| FR | 2770126 B1 | 2/2000 |
| WO | 2004112841 A2 | 12/2004 |

* cited by examiner

DENTAL SCREW

TECHNICAL FIELD

The disclosure relates to a bioresorbable screw for fixing an implant, which may be used specifically in the field of dentistry. In particular, the disclosure relates to screws for fixing bioresorbable membranes and implants that are used to fill bone defects. The disclosure further relates to a set with an implant and at least one bioresorbable screw.

BACKGROUND

Bioresorbable implants, such as collagen films in particular, are usually fastened in practice with nails or wires, which have to be explanted elaborately after the implant has been dissolved.

Bioresorbable screws offered on the market, such as those used for bone plates, for example, are generally not well-suited for anchoring implants in the area of the jaw. In particular, most screws available on the market are designed to attach a solid and rigid component and are therefore not well-suited for fixing thin flexible sheets, such as films or membranes made of collagen, or for porous mouldings.

SUMMARY

Against this background, the object of the disclosure is to provide a screw which is formed to be bioresorbable on the one hand and which, on the other hand, allows for good manageable, secure attachment of implants that do not consist of a solid, rigid material.

The object of the disclosure is achieved by a screw for fixing an implant as claimed.

Preferred embodiments and further developments are evident from the subject matter of the dependent claims, the description and the drawings.

The disclosure relates to a screw for fixing an implant. In particular, the disclosure relates to a screw for use in the field of dentistry, in particular in the field of oral surgery.

However, it is quite possible to use the disclosed screw for affixing tendons or ligaments or for affixing small bone fragments, in particular in hand and foot surgery as well. A use in bony tendon tears, in the fixation of the capsule in rhizarthrosis or during the insertion of a spacer is conceivable as well. The screw could also be used on the hip or shoulder or in knee arthroscopy.

Further areas of use are the attachment of blocks of bone replacement material or blocks of sintered magnesium particles and/or sintered magnesium fibres, which can be introduced into defect sites and which are intended to promote bone growth.

A use in bone augmentation is conceivable as well.

The screw consists of a bioresorbable material.

Preferably, the screw consists of a metal, in particular of magnesium or of a magnesium alloy.

In a preferred embodiment, the screw consists of a magnesium alloy containing yttrium, zinc, manganese and/or calcium, in particular as main alloy components. Yttrium-containing magnesium alloys have improved properties in terms of corrosion, i.e. the screws corrode more slowly as compared to pure magnesium.

The screw has a thread for screwing it into the bone and a head with a drive and with a cap. The cap comprises a contact surface, which is preferred to be substantially flat, for the implant. A predetermined breaking point exists between the drive and the cap.

Thus, to allow for easy insertion of the screw, the drive is connected to a handling tool such as an electrically or pneumatically operated screwdriver (e.g. a slow rotating dental drill) or a mechanical screwdriver.

Drive and tool are preferably designed appropriately such that the drive is locked in the tool holder, in particular clamped or locked.

In this way, the screw can be screwed in via the handling tool and the drive is removed after the screw is screwed in by breaking it off at the predetermined breaking point, without there being a risk of it falling out.

According to one embodiment, the predetermined breaking point is designed appropriately such that, as soon as the contact surface of the cap comes to rest on the implant and thus blocks the screw from being screwed in further, the drive breaks off due to the torsional moment upon the screw being screwed in further.

Another option is to break off the drive by tilting the handling tool. If, for example, the bone structure in a patent is very soft and the screw threatens to break out, the drive can also be pinched off by means of a tool.

After breaking off the drive, the preferably mushroom-shaped cap sits flat on the implant, such that even fragile or thin implants are attached relatively securely.

In particular, flexible sheet materials such as magnesium and/or collagen films can be securely affixed as well.

According to a preferred embodiment, the predetermined breaking point is designed in the form of a constriction, preferably in the form of a constriction whose smallest diameter is smaller than the smallest diameter of a shaft and/or a root of thread. In particular, the constriction has a diameter of 0.70 to 0.99 times that diameter.

It has been evident that even the diameter of the constriction being 0.90 to 0.99 times the smallest diameter of the shaft or root of thread is sufficient to ensure in each case the breaking-off at the predetermined breaking point, without there being a risk of the screw breaking at another point, in particular in the region of a shaft or the thread.

The cap is preferably designed to be plate-shaped. Preferably, the cap has a maximum height up to the predetermined breaking point of less than 2 mm, particularly preferably of less than 1 mm and most preferably of less than 0.8 mm.

Due to the breakaway drive, a cap with a low height can be provided since it does not need to be provided with interlocking elements for engagement by a tool.

In one embodiment, the smallest diameter of a shaft of the screw is at most as large as the diameter of the root of thread. In particular, the smallest diameter of the shaft is approximately as large as the diameter of the root of thread.

As a result, shaft and root of thread form a circular cylinder, at least in sections thereof. The teeth of the thread flights protrude from said circular cylinder.

Usually, bone screws are held securely only in the cortical bone. Now, if the cortical bone is thin, as occurs often especially in older patients, it may happen that only the shaft, but not the thread is anchored in the cortical bone when the screw is screwed in fully. Accordingly, the thread is screwed through into the cancellous bone and has no support there.

However, since there is now a hole in the cortical bone, whose diameter corresponds approximately to the diameter of the root of thread and which thus only has thread flight that are equivalent to the thread of the screw, the screw, even if it is "screwed through", is secured at least against axial displacement such that it does not fall out even without the thread being jammed in the cortical bone.

In a preferred embodiment, the thread has a self-tapping tip.

In a further embodiment, the screw is designed appropriately such that it can be hammered in. In particular, a tip of the screw has a cone angle of less than 60°, preferably of less than 40°.

The thread is designed to be single-flight according to one embodiment. It is also conceivable to have a further development with a multi-flight, in particular double-flight, thread, in particular in one embodiment, in which the screw can also be hammered in, instead of being screwed in.

In a preferred embodiment, the screw has a self-tapping tip though, which cuts thread flights into the bone tissue when the screw is being screwed in.

Nevertheless, it is preferable to pre-drill before screwing the screw in, in particular with a drill whose diameter differs by a maximum of 25% from the diameter of the root of thread.

However, according to one embodiment, the self-tapping tip is designed appropriately such that a blade is present only in an edge region, but not in a centre of the tip.

In particular, the at least one blade of the self-tapping tip extends over a range of 10 to 80%, preferably of 20 to 60%, of the external diameter of the thread.

As a result, the self-tapping thread of the screw does not have to perform all of the drill activity, which reduces the torques occurring while the screw is being screwed in.

Furthermore, as provided in one embodiment, the screw may be provided with a centring cone, in the region of which no blade is arranged. This allows the screw to be easily inserted and centred in the borehole.

In another embodiment, the self-tapping tip extends to the front end of the screw. This embodiment is particularly well-suited for screw that can be hammered in.

According to one embodiment, the cap has a diameter of 1 to 6 mm, preferably of 2 to 4 mm.

Preferably, the cap has a diameter that is 1.5 to 5 times, particularly preferably 2 to 4 times the diameter of the shaft and/or of the root of thread.

The pitch of the thread is preferably 0.5 to 1.6 mm. In an embodiment, in which the screw can be hammered in, the pitch is preferably larger than 1.6 mm, in particular 1.6 to 2.5 mm.

According to a preferred embodiment, the teeth of the thread are designed to be flat or rounded on the outside.

The teeth of the thread can be designed appropriately such that the tooth base merges rounded into the tooth flanks.

In particular, the thread is designed as a single- or double-flight trapezoidal thread with a rounded tooth base. Preferably, the tooth flanks merge into the tooth tips in a rounded manner.

This prevents the thread from having sharp edges that corrode more quickly after implantation.

In particular, the width of the teeth is at least 0.5 times, preferably 0.7 times the width of the tooth base.

In a further development, the screw has a coating. In particular, the screw has a coating made of magnesium fluoride. Such a passivating coating, which inhibits corrosion in the initial time after insertion, can be easily provided by immersing a screw made of magnesium or a magnesium alloy in hydrofluoric acid.

In particular, enhanced corrosion due to a higher chloride concentration of a saline-swollen collagen membrane that is attached by means of the screw is reduced.

Likewise, the formation of galvanic cells due to adjacent metals and the associated increased initial corrosion can be reduced.

The invention further relates to a screw, in particular a screw with one or more of the features described above.

In particular, the screw consists of a bioresorbable material and comprises a thread for screwing it into the bone.

Furthermore, the screw may or may not comprise a breakaway drive.

The screw further includes a shaft adjacent to which there is a head with a cap.

According to the further aspect, the cap has a contact surface, which is preferred to be essentially flat, for the implant, whereby the shaft thickens towards the cap, which forms the head of the screw, possibly together with the drive.

The shaft is therefore thicker in a region directly below the cap than in the region adjacent thereto in the direction of the thread.

As a result, the thickened region touches against the upper side of the implant at the end of the process of screwing in the screw, such that the torque required to screw the screw in further is suddenly increased and the screw is not screwed in further by the user.

This ensures that the contact surface of the cap is not exposed to pressure so strongly such that it is damaged while the screw is screwed in onto the implant.

This applies in particular to implants which are designed as flexible sheet-like structures.

Due to the thickening below the cap, a gap is created, as it were, between the bone and the contact surface, in which the sheet-like structure is seated.

The thickened region is designed appropriately, in particular, such that the shaft has a conical section adjacent to the head. This results in a jamming of the screw at the end of the process of screwing the screw in process, whereby the cap of the screw is still at a distance from the cortical bone and therefore the implant is prevented from being punched by the cap.

Accordingly, a conical section does not lead to a step in the implant, but usually to an expansion of the borehole until the clamp jams. As a result, the torques that can be transmitted to the implant via the contact surface in the sense of a friction clutch and thus can lead to a punching while the screw is being screwed in, are reduced.

The conical section can be designed, in particular, to be truncated cone-shaped.

In a further development, the angle of the cone-shaped section becomes steeper in a transition region of the cap, with respect to a central axis. In particular, the transition region between the cone-shaped section and the adjacent cap is designed as a radius.

As a result, the diameter of the shaft increases sharply right in front of the contact surface, such that the screw is fixed, at the latest when this area comes into contact with the implant.

The transition region preferably has a length of 0.5 to 2 mm (along the central axis of the screw). Thus, the screw is particularly well-suited for the fixation of sheet-like structures as implants.

According to one embodiment, the cone-shaped section may comprise a surface line, with respect to a central axis, that extends at an (mean) angle of 20 to 40°, preferably of 35 to 45°, with respect to the central axis of the screw. Preferably, the cone-shaped section has an axial length of 0.2 to 10 mm, preferably of 0.4 to 0.6 mm.

Preferably, the cone-shaped section has a largest diameter that is 1.1 to 2.5, particularly preferably 1.3 to 1.8 times larger than the smallest diameter of the shaft.

The invention further relates to a kit with at least one screw of the type described above and an implant.

The implant is designed, in particular, as a flexible sheet-like structure, in particular as a collagen membrane and/or magnesium foil.

The kit may further comprise, as provided according to one embodiment, a pilot drill, which preferably has approximately the same diameter as the shaft and/or the diameter of the root of thread of the screw.

Depending on the condition of the bone substance, a pilot drill can be used for pre-drilling that has a smaller diameter than the diameter of the root of thread or the pre-drilling can even be dispensed with, especially in case of the embodiment of the screw that can be hammered in.

The kit may further include a holder for a plurality of screws and/or a template for positioning the pilot drill. The holder serves for intermediate storage of the screws and is preferably sterilisable. In particular, the holder consists of a metal-free sterilisable material, e.g. of a polysiloxane. This allows the screws to be taken up in sterile condition without touching them.

Further, the kit may include an adapter for a screw that comprises a coupling for connection to a handpiece for manual screwing in of the screws or to a dental drill.

BRIEF DESCRIPTION OF THE DRAWINGS

The invention shall be illustrated in more detail in the following through reference being made to exemplary embodiments based on the drawings FIG. 1 to FIG. 9.

FIG. 8 and FIG. 9 show an embodiment of a screw that can be hammered in.

DETAILED DESCRIPTION

Figure 1:
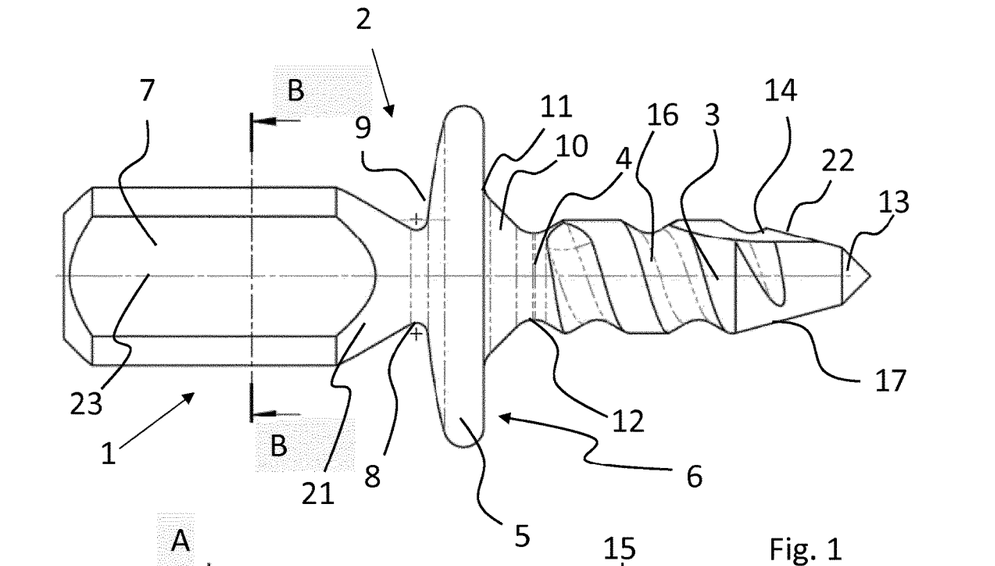
FIG. 1 is a side view of a first embodiment of a screw, which is designed in particular for oral surgery, in particular for attaching sheet-like structures, such as collagen membranes or magnesium foils.

FIG. 1 is a side view of a screw 1 according to a first exemplary embodiment.

Figure 5:
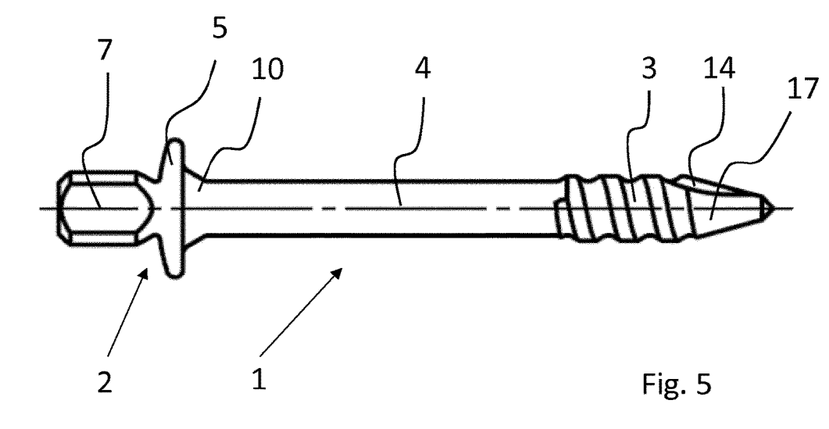
FIG. 5 is a sectional view of another exemplary embodiment of a screw. This is designed to be longer and in particular for attachment of blocks that are used to fill bone defects.
Figure 6:
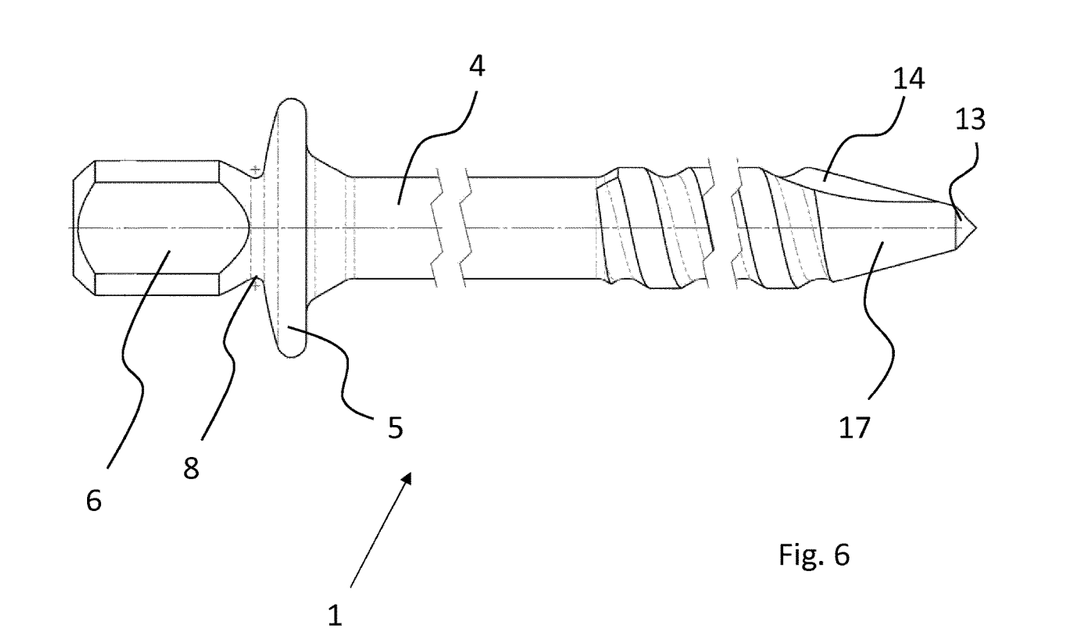
FIG. 6 is a magnified view of FIG. 5.

In general, the screws are preferred to have a total length (including head 2 with drive 7) of 3 to 20 mm. The shorter version shown here by comparison to FIG. 5 and FIG. 6 is preferred to have a total length of 5 to 10 mm.

The screw 1 comprises a head 2, which consists of the cap 5 and the drive 7. Adjacent to the head 2, there is a shaft 4 which merges directly into the thread 3 in the present exemplary embodiment.

The cap 5 is designed to be plate-shaped and is rounded at the top 9 in the present embodiment.

The bottom side forms a preferably flat contact surface 6 which secures the implant when used as intended.

The drive 7 is adjacent to the cap 9.

The drive 7 can be used to insert the screw 1 into a handling tool (not shown). The drive 7 is preferably secured by the handling tool such that it cannot fall out.

Between the top side 9 of the cap 5 and the drive 7, there is a constriction that forms a predetermined breaking point 8.

The diameter of the screw 1 is the smallest in the region of the predetermined breaking point 8.

In particular, the predetermined breaking point 8 can comprise a diameter that is 5 to 10% smaller than the thinnest point of the shaft 4 or of the diameter of the root of thread of thread 3.

The breaking point 8 is located directly adjacent to the cap 5 such that only the cap 5, which is then flat, remains after the drive 7 is broken off.

From the predetermined breaking point 8, which may be designed in particular as a radius, the diameter of the screw 1 increases in the direction of the drive 7, in this embodiment in the form of a truncated cone in the region 21 with a point angle of for example 40 to 80°.

The thread 3 is designed to be single-flight. The thread flight 16 preferably runs less than 10, particularly preferably less than 6, times around the core. This allows the screw 1 to be screwed in by few turns.

The tip 17 of the screw 1 is designed to be self-tapping on the one hand and is provided with the blade 14. The thread flights are made in the bone by means of the blade 14 when the screw 1 is being screwed into a pre-drilled drill hole.

Moreover, the tip 17 has a centring cone 13 which has a surface line in the present exemplary embodiment that has a steeper angle with respect to the central axis 23 of the screw 1 than the cutting edge 22 of the blade 14.

The cutting edge 22 can, in particular, have an angle of 10 to 30° with respect to the central axis 23.

In the present exemplary embodiment, the thread 3 extends almost to the head 2 of the screw 1. In the present exemplary embodiment of a screw 1, the cone-shaped section 10 of the shaft 4 is directly adjacent to the thread 3.

Adjacent to the bottom side, i.e. the contact surface 6 of the cap 5, the diameter of the shaft 4 increases originating from the thread 3 in the direction of the cap 5.

The present exemplary embodiment provides a cone-shaped section 10, which preferably has a surface line with an angle of 20 to 40° with respect to the central axis 23.

The diameter of the shaft 4 increases in the region of the cone-shaped section 10, preferably to be 1.2 to 1.7 times the smallest diameter of the shaft 4 and/or of the core diameter of the thread 3.

The transition area 11 from the cone-shaped section 10 of the shaft toward the head 2 is designed as a radius in this embodiment.

In the transition area 11, which can have a radius, in particular, of 0.1 to 0.5 mm, the diameter increases abruptly such that the screw 1 is stopped at the latest by said transition area 11 when it is being screwed in.

The thread-side transition area 12 of the cone-shaped section 10 is preferably designed to be rounded.

As a result, in particular during the attachment of flexible sheet-like structures such as collagen membranes or films, the contact surface 6 is prevented from pressing onto the implant in a manner leading to punching.

The diameter of the cap 5 preferably is 2 to 4 mm, the diameter of the shaft preferably is 0.6 to 1.5 mm.

The centring cone 13 can comprise a point angle of 70 to 110°.

The thread of the bone screw according to the invention preferably has a length of 2 to 18 mm, in the present embodiment of a short screw preferably of 2 to 5 mm.

Preferably, the thread flight 16 runs less than five, particularly preferably less than four times about the screw 1. Accordingly, the screw can be screwed in with just a few turns.

Figures 2, 3, 4:
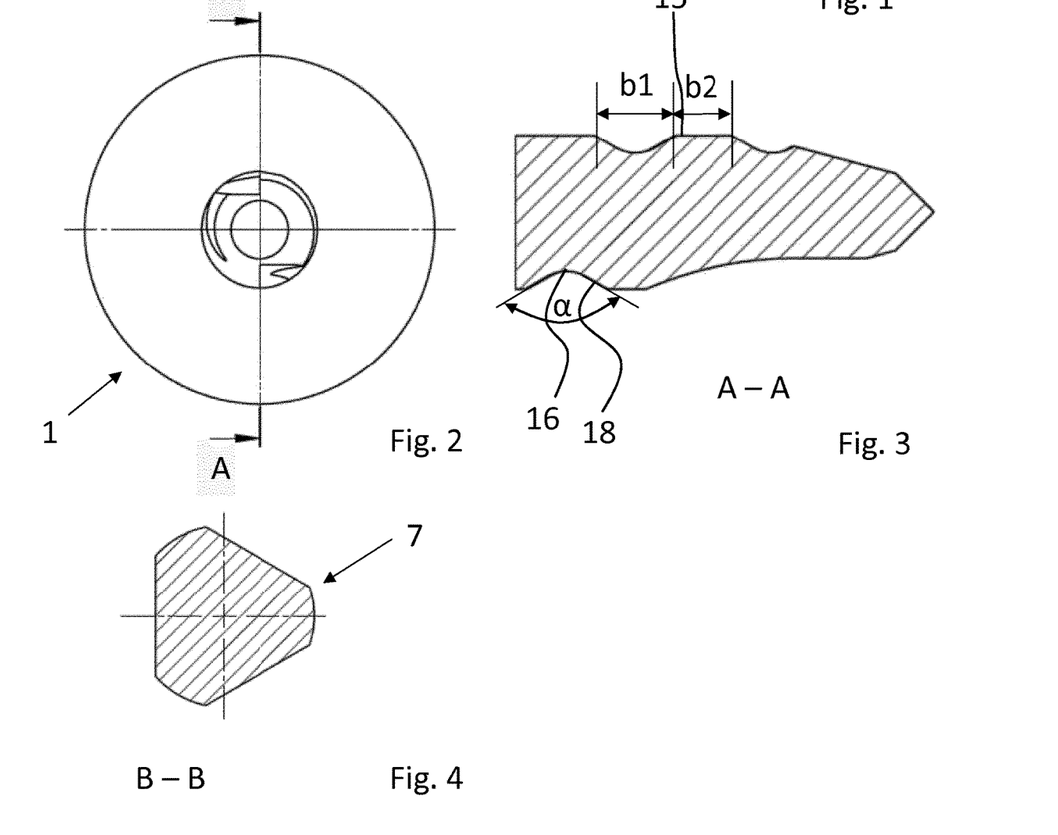
FIG. 2 is a top view onto the tip of the screw.
FIG. 3 is a sectional view along A-A according to FIG. 2.
FIG. 4 is a sectional view along B-B of FIG. 1.

FIG. 2 shows a top view onto the tip of the screw 1.

FIG. 3 is a detail view of a section along the line A-A of FIG. 2.

It is evident herein that the thread flights 16 are designed as rounded depressions whose flanks 18 preferably have a flank angle α of 90 to 150°. The thread teeth 15 are preferably designed to be flat, in particular, these have an axial length of 0.2 to 0.5 mm.

The thread 3 is designed in this exemplary embodiment as a single-flight trapezoidal thread with rounded tooth base.

The width b1 of a thread tooth 15 can be at least 0.5 times the width b2 of the tooth base (including tooth flanks).

The thread teeth 15 do not form a tip, since a tip would initially be exposed to high corrosion and thus the strength of the screw connection would diminish too quickly.

FIG. 4 is a sectional view along the line B-B of FIG. 1.

The drive 7 is designed in this embodiment to be triangular in cross-section with rounded tips. It shall be understood, however, that the geometry of the drive 7 is quite arbitrary. It only has to ensure the transmission of sufficient torque. Thus, for example, a hexagonal or a star-shaped embodiment is conceivable as well (not shown).

FIG. 5 is a side view of an alternative embodiment of a screw that is longer than the screw shown in FIG. 1 to FIG. 4. It has a total length of preferably more than 8, particularly preferably of more than 12 mm.

The screw 1 comprises a head 2 comprising the drive 7 and the flat cap 5 in this exemplary embodiment as well.

The shaft 4 of the screw 1 that is not provided with a thread in this exemplary embodiment is at least twice, preferably at least three times as long as the thread 3. Shaft 4 and thread 3, taken together, preferably are between 8 and 18 mm in length.

Otherwise, the screw is designed similar to the screw shown with reference to FIG. 1 to FIG. 4, and also comprises, in particular, the cone-shaped section 10 at the head end of the shaft 4 as well as the tip 17 with a blade 14.

FIG. 6 is a detail view of FIG. 5 from which is evident that the long version of a screw 1 shown therein is essentially equivalent in terms of design to the shorter version according to the drawings of FIG. 1 to FIG. 4.

However, the shaft 4 of the screw 1 as well as the core diameter of the thread 3 are preferred to be somewhat thicker. It has a diameter, in particular, of 1.0 to 1.3 mm.

It has been evident that even a constriction with a slightly smaller diameter than the shaft 4, in particular a diameter smaller by 0.01 to 0.05 mm, leads to a sufficiently secure predetermined breaking point 8.

The tip 17 is also designed according to FIG. 1 and comprises a blade 14 for introducing the thread flights as well as a centring cone 13 without blade.

Figure 7:
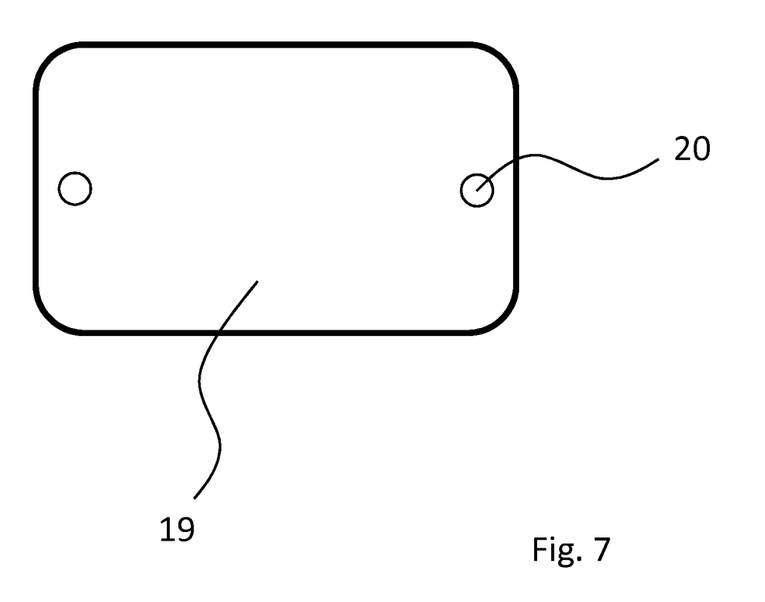
FIG. 7 schematically shows how an implant can be attached with one of the screws.

FIG. 7 is a schematic view of an implant 19 that is designed as a sheet-like structure, for example as collagen film. Same is placed on the wound for covering, for example, a bone defect. Subsequently, a drill is used to introduce drill holes 20, which essentially correspond to the diameter of the shaft of the screw and/or the diameter of the thread core.

Subsequently, the implant 19 is attached with at least one screw.

In this context, the screw is rotated into the drill hole 20 until the rotation is stopped at the end of the cone-shaped section (10 in FIG. 1 and FIG. 6).

The drive then breaks off either because of the torque while the screw is being screwed in, when the head of the screw comes into contact with the implant and/or the bone. But the user can just as well break off the drive by snapping it off.

The screws preferably consists of a magnesium alloy. In the case of using a magnesium foil as an implant 19, the voltage difference being no more than small, there is no increased corrosion such that both implant 19 as well as the screw degrade only after healing.

Figure 8:
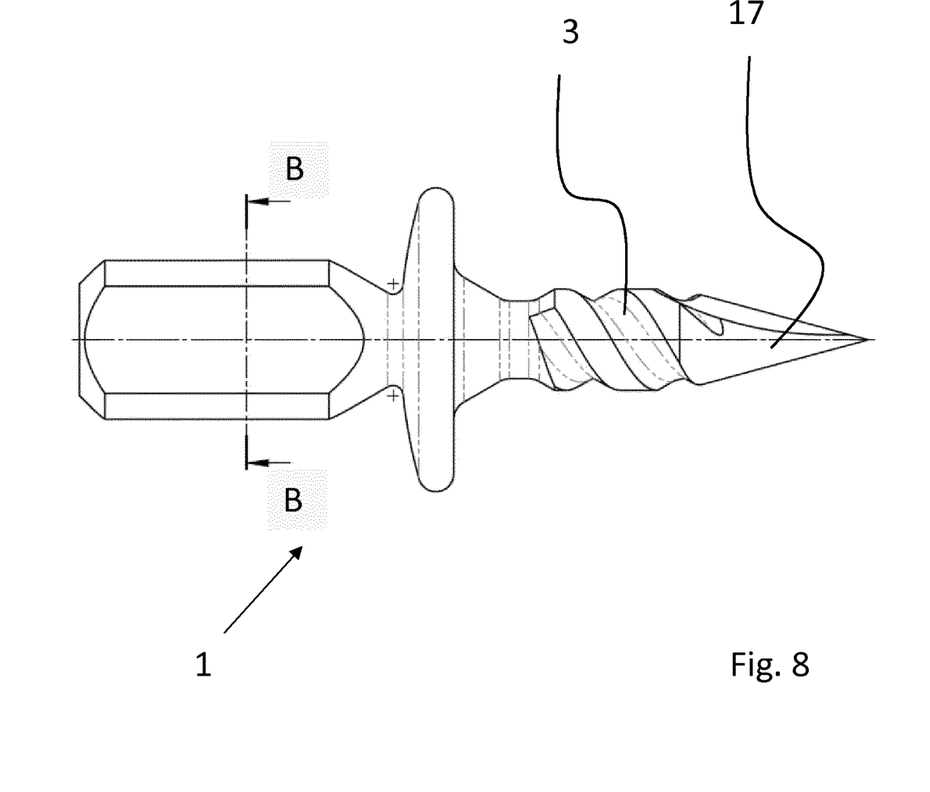
Figure 9:
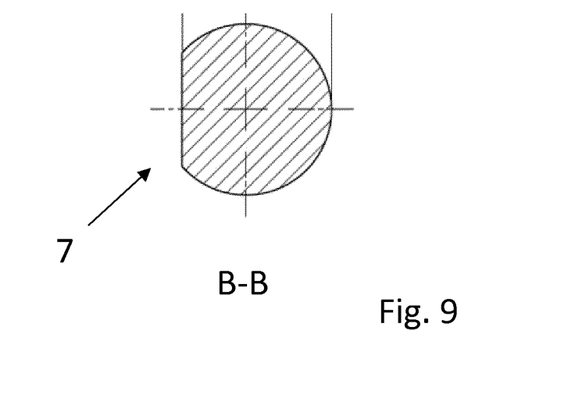

FIG. 8 and FIG. 9 show an alternative embodiment of a screw 1, which can be hammered in as well.

As shown in FIG. 8, the self-tapping tip 17 extends to the front end of the screw 1. The self-tapping tip 17 has a cone angle of less than 45°, preferably of less than 40°. A separate centring cone with a different cone angle (13) in FIG. 1) is not provided.

Moreover, the thread 8 is designed to be multi-flight, in particular double-flight, and has a greater pitch than the thread of the embodiments according to FIG. 1 to FIG. 6.

FIG. 9 is a sectional view along the line B-B of FIG. 8. The drive 7 has a different geometry than the drive according to FIG. 1 to FIG. 6, namely the geometry of a circular cylinder sectioned on one side. However, it is obvious that the drive can just as well comprise the geometry shown in FIG. 4.

Otherwise, the screw shown in FIG. 8 and FIG. 9 is essentially equivalent to the exemplary embodiment according to FIG. 1.

Figure 10:
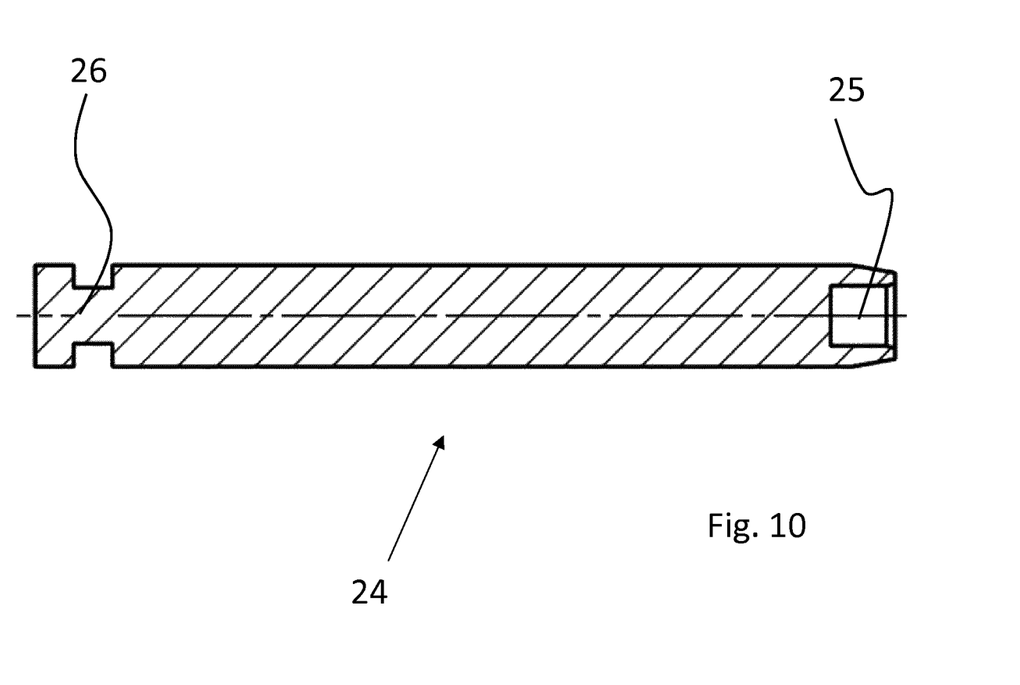
FIG. 10 and FIG. 11 show an adapter for one of the screws that can be coupled to a dental drill or a manual screwdriver.

FIG. 10 is a sectional view of an adapter 24 for a screw which can be placed onto a dental drill or manual screwdriver (not shown).

For this purpose, the adapter 24 comprises a coupling 26 that can be connected to the dental drill or manual screwdriver and can be of any design such as to be adapted to the drill or screwdriver used in this context.

Moreover, the adapter, in particular similar to a bit holder, comprises a holder 25 for the drive of a screw.

Figure 11:
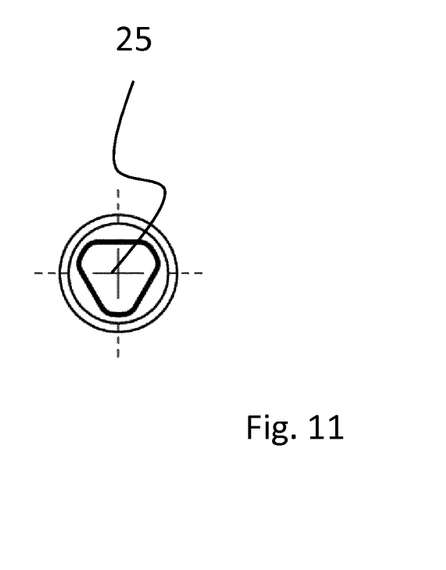

As is evident from the top view onto the front face according to FIG. 11, the geometry of the holder 25 in the present exemplary embodiment is adapted to the geometry of the drive of the screw shown in FIG. 4.

Preferably, the drive of the screw can be jammed or snapped in within the holder 25. Once the screw is screwed in fully, the broken-off drive remains in the holder 25.

According to one embodiment (not shown), the drive can then be ejected by means of a handling organ, e.g. by a pin that can be axially displaced in the adapter 24 and pushes the drive out, or by release of a latching mechanism.

The invention provides for simple and reliable attachment, in particular of dental implants.

LIST OF REFERENCE NUMBERS

1 Screw
2 Head
3 Thread
4 Shaft
5 Cap
6 Contact surface
7 Drive
8 Predetermined breaking point
9 Top side
10 Cone-shaped section
11 Transition area
12 Transition area
13 Centring cone 14 Blade
15 Thread tooth
16 Thread flight
17 Tip
18 Flank
19 Implant
20 Bore hole
21 Region
22 Cutting edge
23 Central axis
24 Adapter
25 Holder
26 Coupling

The invention claimed is:

1. A screw for fixing an implant,
wherein the screw consists of a bioresorbable material,
wherein the screw comprises a thread for screwing it into a bone,
wherein the screw comprises a head with a cap and a drive,
wherein the cap comprises an essentially flat contact surface for the implant,
wherein a predetermined breaking point that is designed as a constriction between a top side of the cap and the drive is present between the drive and the cap, and
wherein a shaft of the screw thickens towards the cap, and
wherein teeth of the thread comprise a width that is at least 0.5 times a width of a tooth base.

2. The screw according to claim 1, wherein the cap is provided to be plate-shaped.

3. The screw according to claim 2, wherein the cap comprises a maximum height up to the predetermined breaking point of less than 2 mm.

4. The screw according to claim 2, wherein the cap comprises a maximum height up to the predetermined breaking point of less than 0.8 mm.

5. The screw according to any claim 1,
wherein the screw comprises a shaft, and
wherein a smallest diameter of the shaft is at most as large as a core diameter of the thread.

6. The screw according to any claim 1,
wherein the screw comprises a shaft, and
wherein a smallest diameter of the shaft is equivalent to a core diameter of the thread.

7. The screw according to claim 1, wherein the thread has a self-tapping tip.

8. The screw according to claim 1, wherein at least one of the following applies:
the cap has a diameter of 1 to 6 mm;
a diameter of the cap is 1.5 to 5 times a diameter of the shaft and/or a core of the thread;
a pitch of the thread is 0.5 to 1.6 mm;
the teeth of the thread are designed to be flat on the outside;
the teeth of the thread are designed such that bases of the teeth merge rounded into flanks of the teeth;
the screw comprises a centring tip.

9. The screw according to claim 1, wherein the screw consists of magnesium or of a magnesium alloy.

10. The screw according to claim 1, wherein the screw consists of a magnesium alloy containing yttrium, zinc, manganese and/or calcium.

11. The screw according to claim 1, wherein the screw comprises a coating made of magnesium fluoride.

12. The screw according to claim 1, wherein the shaft comprises a cone-shaped section adjacent to the head.

13. The screw according to claim 12, wherein an angle of the cone-shaped section becomes steeper in a transition region towards the cap, with respect to a central axis.

14. The screw according to claim 13, wherein the transition region has a length of 0.5 to 2 mm.

15. The screw according to claim 1, wherein the screw comprises, below the cap, a cone-shaped section which is at an angle of 20 to 40° with respect to a central axis of the screw, and/or which has a length of 0.2 to 10 mm.

16. A kit including at least one screw according to claim 1 and an implant that is designed as a sheet-like structure.

17. The kit according to claim 16, further comprising
a pilot drill, which has approximately a same diameter as the shaft of the screw, and/or
an adapter for holding a screw, wherein the adapter comprises a coupling for connection to a handpiece or to a dental drill, and/or
a holder for a plurality of screws.

18. A screw for fixing an implant,
wherein the screw consists of a bioresorbable material, namely of magnesium or of a magnesium alloy,
wherein the screw comprises a thread for screwing it into a bone, wherein the screw comprises a head with a cap and a drive,
wherein the cap comprises an essentially flat contact surface for the implant,
wherein a predetermined breaking point that is designed as a constriction between a top side of the cap and the drive is present between the drive and the cap,
wherein a shaft of the screw thickens towards the cap,
wherein the thread is designed such that teeth of the thread are flat or rounded on the outside and bases of the teeth merge rounded into flanks of the teeth, and
wherein the thread has a self-tapping tip, wherein teeth of the thread comprise a width that is at least 0.5 times a width of a tooth base.

* * * * *